US00PP18963P2

(12) United States Plant Patent
Yomo et al.

(10) Patent No.: US PP18,963 P2
(45) Date of Patent: Jun. 24, 2008

(54) ***VERBENA* PLANT NAMED 'SUNTAPIPA'**

(50) Latin Name: *Verbena hybrida*
Varietal Denomination: Suntapipa

(75) Inventors: Yasunori Yomo, Kanagawa (JP); Naoto Takamura, Yamanashi (JP)

(73) Assignee: Suntory Flowers Ltd, Tokyo (JP)

( * ) Notice: Subject to any disclaimer, the term of this patent is extended or adjusted under 35 U.S.C. 154(b) by 28 days.

(21) Appl. No.: 11/583,639

(22) Filed: Oct. 19, 2006

(51) Int. Cl.
*A01H 5/00* (2006.01)

(52) U.S. Cl. ..... Plt./308
(58) Field of Classification Search ..... Plt./308
See application file for complete search history.

*Primary Examiner*—Kent L. Bell
(74) *Attorney, Agent, or Firm*—C. A. Whealy

(57) ABSTRACT

A new and distinct cultivar of *Verbena* plant named 'Suntapipa', characterized by its outwardly spreading to trailing plant habit; vigorous growth habit; freely branching habit; freely flowering habit; and intense violet-colored flowers that are held above and beyond the foliage.

1 Drawing Sheet

Botanical designation: *Verbena hybrida.*
Cultivar denomination: 'Suntapipa'.

BACKGROUND OF THE INVENTION

The present invention relates to a new and distinct cultivar of *Verbena,* botanically known as *Verbena hybrida,* and hereinafter referred to by the name 'Suntapipa'.

The new *Verbena* is a product of a planned breeding program conducted by the Inventors in Shiga, Japan. The objective of the breeding program is to create new *Verbena* cultivars with large inflorescences and attractive flower coloration.

The new *Verbena* originated from a cross-pollination made by the Inventors in March, 1999 in Shiga, Japan of a proprietary seedling selection of *Verbena hybrida* identified as code number T86-99-2, not patented, as the female, or seed, parent with a proprietary seedling selection of *Verbena hybrida* identified as code number T85-99-2, not patented, as the male, or pollen, parent. The new *Verbena* was discovered and selected by the Inventor as a single flowering plant within the progeny of the stated cross-pollination in a controlled environment in Shiga, Japan.

Asexual reproduction of the new *Verbena* by terminal cuttings in a controlled environment in Shiga, Japan since October, 2001 has shown that the unique features of this new *Verbena* are stable and reproduced true to type in successive generations.

SUMMARY OF THE INVENTION

The cultivar Suntapipa has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Suntapipa'. These characteristics in combination distinguish 'Suntapipa' as a new and distinct cultivar of *Verbena:*

1. Outwardly spreading to trailing plant habit.
2. Vigorous growth habit.
3. Freely branching habit.

4. Freely flowering habit.
5. Intense violet-colored flowers that are held above and beyond the foliage.

Plants of the new *Verbena* can be compared to plants of the female parent selection. Plants of the new *Verbena* differ from plants of the female parent selection in the following characteristics:

1. Plants of the new *Verbena* have larger flowers than plants of the female parent selection.
2. Plants of the new *Verbena* have larger inflorescences than plants of the female parent selection.
3. Plants of the new *Verbena* and the female parent selection differ in flower coloration.

Plants of the new *Verbena* can be compared to plants of the male parent selection. Plants of the new *Verbena* differ from plants of the male parent selection in the following characteristics:

1. Plants of the new *Verbena* have shorter lateral branches than plants of the male parent selection.
2. Plants of the new *Verbena* and the male parent selection differ in flower color as plants of the male parent selection have lighter colored flowers.

Plants of the new *Verbena* can be compared to plants of the *Verbena* cultivar Sunmaref TP-V, disclosed in U.S. Plant Pat. No. 9,411. In side-by-side comparisons conducted in Shiga, Japan, plants of the new *Verbena* differed from plants of the cultivar Sunmaref TP-V in the following characteristics:

1. Plants of the new *Verbena* were not as broad as plants of the cultivar Sunmaref TP-V.
2. Plants of the new *Verbena* had shorter lateral branches and internodes than plants of the cultivar Sunmaref TP-V.
3. Plants of the new *Verbena* had larger flowers than plants of the cultivar Sunmaref TP-V.
4. Plants of the new *Verbena* and the cultivar Sunmaref TP-V differed in flower color as plants of the cultivar Sunmaref TP-V had purple-colored flowers.
5. Plants of the new *Verbena* had shorter peduncles than plants of the cultivar Sunmaref TP-V.

BRIEF DESCRIPTION OF THE PHOTOGRAPHS

The accompanying colored photographs illustrate the overall appearance of the new *Verbena,* showing the colors as true as it is reasonably possible to obtain in colored reproductions of this type. Colors in the photographs may differ slightly from the color values cited in the detailed botanical description which accurately describe the colors of the new *Verbena*.

The photograph at the top of the sheet comprises a side perspective view of a typical flowering plant of 'Suntapipa' grown in a container.

The photograph at the bottom of the sheet is a close-up view of typical inflorescences of 'Suntapipa'.

DETAILED BOTANICAL DESCRIPTION

The aforementioned photographs and following observations and measurements describe plants grown in Shiga, Japan, under commercial practice during the spring in an outdoor nursery with day temperatures averaging 21° C. and night temperatures averaging 14° C. Plants were grown with one rooted cutting per 13.5-cm container for about four months and were pinched one time. In the following description, color references are made to The Royal Horticultural Society Colour Chart, 2001 Edition, except where general terms of ordinary dictionary significance are used.

Botanical classification: *Verbena hybrida* cultivar Suntapipa.

Parentage:

*Female, or seed, parent.*—Proprietary seedling selection of *Verbena hybrida* identified as code number T86-99-2, not patented.

*Male, or pollen, parent.*—Proprietary seedling selection of *Verbena hybrida* identified as code number T85-99-2, not patented.

Propagation:

*Type.*—By terminal cuttings.

*Time to initiate roots.*—About 10 to 14 days at 15° C. to 20° C.

*Time to produce a rooted young plant.*—About 30 days at 15° C. to 20° C.

*Root description.*—Fine, fibrous; ivory in color.

*Rooting habit.*—Freely branching.

Plant description:

*Plant habit.*—Initially upright, then outwardly spreading to trailing growth habit; lateral branches decumbent. Freely branching habit with about 48 lateral branches developing per plant; pinching enhances lateral branch development. Vigorous growth habit.

*Plant height.*—About 5.6 cm.

*Plant diameter.*—About 38.8 cm.

Lateral branch description:

*Length.*—About 13.2 cm.

*Diameter: About* 1.3 mm.

*Internode length.*—About 1.7 cm.

*Strength.*—Strong.

*Texture.*—Pubescent.

*Color.*—145A.

Foliage description:

*Arrangement.*—Opposite, simple.

*Length.*—About 3.6 cm.

*Width.*—About 2.5 cm.

*Shape.*—Deeply dissected.

*Apex.*—Acute.

*Base.*—Truncate.

*Margin.*—Pinnately parted.

*Texture, upper and lower surfaces.*—Coarse; pubescent.

*Venation pattern.*—Pinnate; reticulate.

*Color.*—Developing and fully expanded foliage, upper surface: 137A; venation, 144D. Developing and fully expanded foliage, lower surface: 138B; venation, 144D.

*Petiole.*—Length: About 1.2 cm. Diameter: About 1 mm. Texture, upper and lower surfaces: Pubescent. Color, upper and lower surfaces: 144B.

Flower description:

*Flower arrangement and habit.*—Salverform flowers arranged in hemispherical terminal racemes; flowers face mostly upright. Freely flowering habit with about 15 flowers per inflorescence.

*Natural flowering season.*—Plants flower continuously from spring to late autumn in Japan.

*Flower longevity.*—Flowers last about one week on the plant. Flowers not persistent.

*Fragrance.*—None detected.

*Inflorescence height.*—About 3.3 cm.

*Inflorescence diameter.*—About 4.6 cm.

*Flowers.*—Appearance: Flared trumpet, corolla fused, five-parted. Diameter: About 1.6 cm. Depth (height): About 1.6 cm. Tube length: About 1.5 cm. Tube diameter: About 1.4 mm.

*Flower buds.*—Length: About 1 cm. Diameter: About 1.3 mm. Shape: Clavate. Color: N87A.

*Corolla.*—Arrangement: Single whorl of five fused petals. Petal length: About 7.2 mm. Petal width: About 7 mm. Petal lobe shape: Obcordate. Petal lobe apex: Cordate. Petal margin: Entire. Petal texture, upper and lower surfaces: Smooth, glabrous; velvety. Color: Petal, when opening and fully opened, upper surface: N81A. Petal, when opening and fully opened, lower surface: N81C. Throat: 155C. Tube: 85A; becoming closer to 155C.

*Calyx.*—Arrangement: One single narrow calyx tube per flower with five fused sepals. Sepal length: About 9 mm. Sepal width: About 1 mm. Sepal shape: Lanceolate. Sepal apex: Acute. Sepal margin: Entire. Sepal texture, upper surface: Smooth, glabrous. Sepal texture, lower surface: Pubescent. Sepal color, upper and lower surfaces: 137C.

*Peduncles.*—Length: About 1.5 cm. Diameter: About 1.2 mm. Strength: Strong. Texture: Pubescent. Color: 144A.

*Pedicels.*—Flowers are sessile.

*Reproductive organs.*—Stamens: Quantity/arrangement: Four per flower, adnate to corolla tube. Anther shape: Ellipsoidal. Anther length: About 1 mm. Anther color: 1A. Pollen amount: Scarce. Pollen color: 1A. Pistils: Quantity: One per flower. Pistil length: About 1.3 cm. Stigma shape: Bi-parted. Stigma color: 145A. Style color: 145C. Ovary color: 144B. Fruits/seed: Fruit and seed development have not been observed.

Temperature tolerance: Plants of the new *Verbena* have been observed to tolerate temperatures from about 0° C. to about 35° C.

Pathogen/pest resistance: Plants of the new *Verbena* have not been observed to be resistant to pathogens and pests common to *Verbenas*.

It is claimed:

1. A new and distinct *Verbena* plant named 'Suntapipa' as illustrated and described.

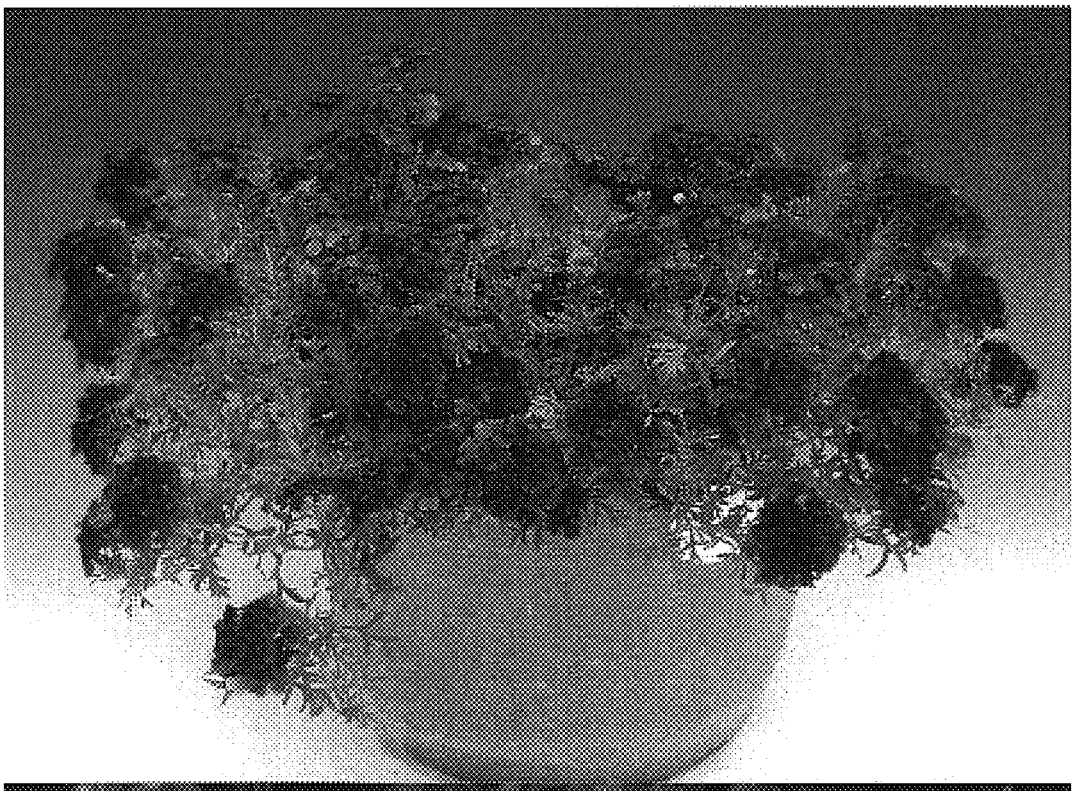
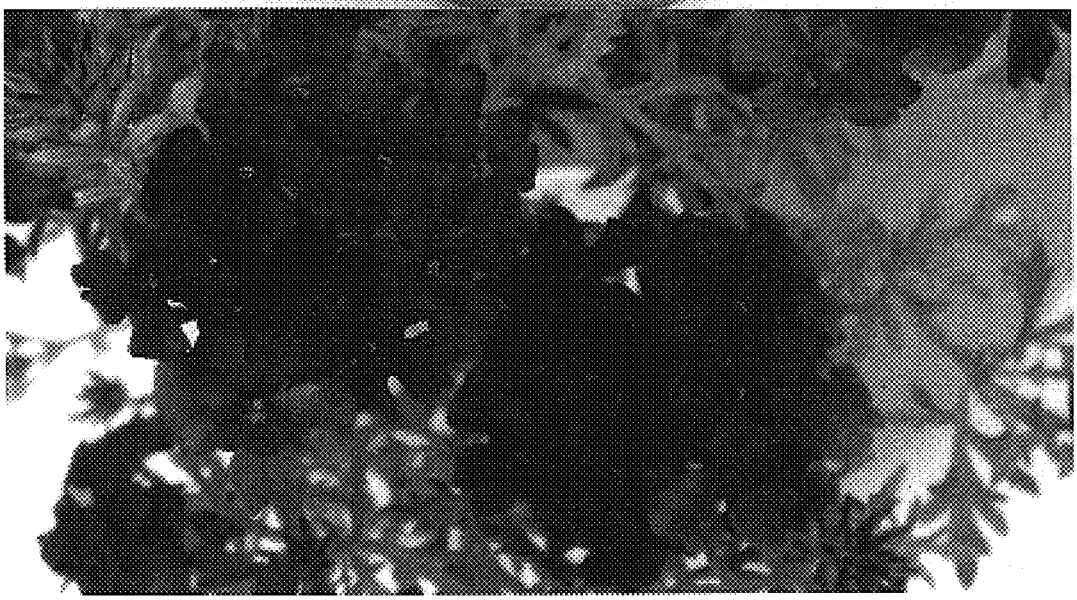

* * * * *